United States Patent [19]

Waller

[11] 4,431,839

[45] Feb. 14, 1984

[54] TOLUIC ACID

[75] Inventor: Francis J. Waller, Wilmington, Del.

[73] Assignee: E. I. Du Pont de Nemours and Company, Wilmington, Del.

[21] Appl. No.: 328,843

[22] Filed: Dec. 9, 1981

[51] Int. Cl.³ .......................................... C07C 51/145
[52] U.S. Cl. ..................................... 562/406; 502/168
[58] Field of Search ........................................ 562/406

[56] References Cited

U.S. PATENT DOCUMENTS

| | | | |
|---|---|---|---|
| 3,700,729 | 10/1972 | Fenton | 260/515 R |
| 3,920,734 | 11/1975 | Ichikawa et al. | 260/515 R |
| 3,965,132 | 6/1976 | Norell | 562/406 |
| 4,076,949 | 2/1978 | Zehner | 560/204 |
| 4,093,647 | 6/1978 | van Venrooy | 260/515 R |
| 4,199,521 | 4/1980 | Kaplan et al. | 260/449 |
| 4,237,071 | 12/1980 | Stapp | 568/401 |
| 4,237,331 | 12/1980 | Stapp | 585/845 |
| 4,262,141 | 4/1981 | Richter et al. | 568/454 |
| 4,281,174 | 7/1981 | Current | 560/204 |

FOREIGN PATENT DOCUMENTS

| | | |
|---|---|---|
| 51-1146430 | 12/1976 | Japan . |
| 1164561 | 9/1969 | United Kingdom . |
| 1485816 | 9/1977 | United Kingdom . |

OTHER PUBLICATIONS

Chem Systems, Inc., Process Evaluation and Research Planning Report, 2nd Quarter, 1976.
Mimoun, et al., J. Am. Chem. Soc., 100, 5437, (1978).
Nyberg, et al., J. Am. Chem. Soc., 103, 4966, (1981).

Primary Examiner—Michael L. Shippen

[57] ABSTRACT

Process for oxidatively carbonylating toluene to toluic acid, at least 50 mol % of the toluic acid being the p-isomer, said process comprising contacting and reacting, at 110°–250° C., at a pressure of at least 500 psi (3.45 MPa), toluene, carbon monoxide, oxygen and the catalyst ingredients consisting essentially of (a) a compound of rhodium or iridium;
(b) a sulfur oxy-acid or a Group Ia or IIa metal salt of a sulfur oxy-acid;
(c) a sulfur oxy-acid or sulfur oxy-acid mixture having a Hammett acidity value ($-H_o$) of greater than 7.0; and
(d) a cupric salt of a sulfur oxy-acid;

said catalyst ingredients containing 0.3–30 mol % of (a) and 70–99.7 mol % of (b+c+d), with the molar ratios (b/a) and (c/a) each being at least 2 and the molar ratio (d/a) being at least 0.5, and recovering toluic acid.

22 Claims, No Drawings

TOLUIC ACID

DESCRIPTION

1. Technical Field

This invention relates to the oxidative carbonylation of aromatic compounds, for example, the preparation of toluic acids from toluene, carbon monoxide and oxygen.

2. Background

The oxidative carbonylation of aromatic compounds to aromatic carboxylic acids is known in the art. U.S. Pat. No. 3,700,729 discloses the catalytic liquid phase process comprising contacting an aromatic compound and carbon monoxide in a substantially anhydrous organic liquid reaction medium which is inert to the reactants and the catalyst which is a halide salt of a Group VIII metal in its highest oxidation state, continuing the contacting until the catalyst is reduced to a lower valence state and the aromatic compound is oxidatively carbonylated, and thereafter hydrolyzing the carbonylated compound to the aromatic carboxylic acid. The patent exemplifies the conversion of toluene to p-toluic acid. U.S. Pat. No. 3,920,734 discloses a process for preparing an aromatic carboxylic acid from an aromatic compound by means of carbon monoxide, oxygen and a palladium carboxylate catalyst. The patent exemplifies the conversion of toluene to a mixture of toluic acid isomers. U.S. Pat. No. 4,093,647 discloses a process for preparing an aromatic carboxylic acid from an aromatic compound of the benzene series by means of carbon monoxide and an inorganic salt mixture consisting of a major amount of a thallium salt and a minor amount of a palladium salt. The patent exemplifies the formation of a mixture of toluic acid isomers, predominantly the p-isomer, from toluene.

The acid-catalyzed carbonylation of aromatic compounds to form aldehydes also is known in the art. Chem Systems, Inc., Process Evaluation and Research Planning Report, 2nd quarter, 1976, discloses the $HF/BF_3$ catalyzed carbonylation of toluene to tolualdehyde which can be converted to terephthalic acid by a liquid phase oxidation. A similar disclosure as to the formation of tolualdehyde is made in British Pat. No. 1,485,816. Japanese Publication J5 No. 1146-430 based on Japanese patent application No. 070587 discloses the formation of tolualdehyde from the reaction of toluene and carbon monoxide in the presence of trifluoromethanesulfonic acid (often referred to as triflic acid) in an anhydrous state or in combination with a Lewis acid.

The use of compounds of rhodium and copper together as catalysts, likewise, is known in the art. For example, Mimoun, et al. in J. Am. Chem. Soc. 100:17 (1978), 5437 disclose the selective oxidation of terminal olefins to methyl ketones by oxygen in the presence of rhodium chloride and cupric nitrate or cupric perchlorate; the copper compound enhances the catalytic efficiency of the rhodium trichloride in the conversion of 1-hexene to 2-hexanone. U.S. Pat. Nos. 4,237,071 and 4,237,331 disclose the use of a catalyst comprising compounds of palladium and copper and a surfactant for the oxidation of olefins to ketones. U.S. Pat. No. 4,262,141 discloses hydroformylation of olefins using rhodium carbonyl complexes containing tertiary phosphine ligands in the presence of a compound of copper, silver or zinc.

The addition of copper salts to improve the conversion of synthesis gas (largely carbon monoxide and hydrogen) to polyhydric alcohols in the presence of a rhodium carbonyl catalyst is known from U.S. Pat. No. 4,199,521. Copper is said to remove the sulfide contaminant from the synthesis gas.

British Pat. No. 1,164,561 discloses the preparation of carbonyl compounds, including carboxylic acids, by reacting an organometallic compound of a Group VIII noble metal (Ru, Rh, Pd, Os, Ir, Pt) with carbon monoxide in a suitable solvent. Water is needed to form a carboxylic acid. Toluene is converted to toluic acids, with 94-96% selectivity to the para isomer. Use of a redox system, particularly copper salts and air, to re-oxidize the Group VIII metal in-situ and increase catalyst efficiency, is disclosed.

U.S. Pat. No. 4,281,174 discloses the preparation of dialkyl oxalates by reacting an alcohol with a mixture of carbon monoxide and oxygen in the presence of a palladium complex, a quinone and a redox agent which can include a copper compound.

U.S. Pat. No. 4,076,949 discloses an oxidative carbonylation of alcohol in the presence of a catalytic mixture of (a) a palladium, rhodium, platinum, copper or cadmium salt; (b) an amine; (c) an oxidant compound comprising a salt of $Cu^{+1}$, $Cu^{+2}$, $Fe^{+2}$ or $Fe^{+3}$; and (d) an ammonium or substituted ammonium salt or acid with a counterion other than halide.

It is an object of this invention to provide a catalytic liquid phase process for producing toluic acids from toluene. A further object is to provide such a process whereby at least 50 mol % of the toluic acids produced is p-toluic acid. Still another object is to provide such a process whereby the yields of the p-isomer are high. Other objects will become apparent hereinafter.

DISCLOSURE OF INVENTION

For further comprehension of the invention, and of the objects and advantages thereof, reference may be made to the following description and to the appended claims in which the various novel features of the invention are more particularly set forth.

This invention provides a process for preparing toluic acid, at least 50 mol % of which is the p-isomer, by reacting toluene, carbon monoxide and oxygen in the presence of a sulfur oxy-acid salt of rhodium or iridium, a cupric salt of a sulfur oxy-acid, and a sulfur oxy-acid having a Hammett acidity ($-H_o$) of greater than 7. More particularly, the invention resides in the process for preparing toluic acid, at least 50 mol % of which is p-toluic acid, by contacting and reacting toluene, carbon monoxide, oxygen and the catalyst ingredients consisting essentially of (a) a compound of rhodium or iridium;
(b) a sulfur oxy-acid or a Group Ia or IIa metal salt of a sulfur oxy-acid;
(c) a sulfur oxy-acid or sulfur oxy-acid mixture having a Hammett acidity value ($-H_o$) of greater than 7.0; and
(d) a cupric salt of a sulfur oxy-acid, preferably of a strong sulfur oxy-acid, for example, sulfuric acid or a sulfonic acid;

said catalyst ingredients containing 0.3-30 mol % of (a) and 70-99.7 mol % of (b+c+d), with the molar ratios (b/a) and (c/a) each being at least 2, preferably at least 3, more preferably at least 4, the molar ratio (d/a) being at least 0.5, preferably at least 4, more preferably at least 8, and recovering toluic acid.

Included under (c) are strong sulfur oxy-acids such as, for example, sulfuric acid ($-H_o$ of 11), oleum and certain sulfonic acids which are also suitable for use under (b). Although not wishing to be bound by this explanation, it is thought that the active catalyst for the oxidative carbonylation reaction consists of one or more ionic species of sulfate or sulfonate of rhodium or iridium and copper, formed by the partial or complete replacement of the anions or ligands of the starting metal compounds with anions from a sulfur oxy-acid or salt thereof, in the presence of strong acid of $-H_o$ greater than 7.0. Evidence for the formation of ionic sulfonates in the reaction of a rhodium compound with a sulfur oxy-acid is provided hereinafter in Example 11. Further evidence is provided in the Procedure for Catalyst Preparation using Nafion ® Perfluorosulfonic Acid Resin described below wherein a reaction between rhodium nitrate, copper nitrate and the polymeric sulfonic acid is followed by titration of the liberated nitric acid and by analysis of rhodium and copper chemically bound to the polymer.

The metal compound which is used as catalyst ingredient (a) can be any rhodium or iridium compound capable of combining chemically with a sulfur oxy-acid or its metal salt. Examples of such compounds include rhodium acetate, trifluoroacetate, chloride and nitrate, the rhodium carbonyls $Rh_6(CO)_{16}$ and $RhH(CO)(P\phi_3)_3$, where $\phi$ is phenyl, and iridium chloride. Examples of suitable sulfur oxy-acids, catalyst component (b), include sulfuric acid; oleum; fluorosulfonic acid; α-fluorosulfonic acids, including trifluoromethanesulfonic acid (triflic acid), perfluorooctanesulfonic acid, and $CF_3CF_2OCF_2CF(CF_3)OCF_2CF_2SO_3H$ (perfluoro-4-methyl-3,6-dioxaoctanesulfonic acid); methanesulfonic acid; benzenesulfonic acid; and p-toluenesulfonic acid. Examples of sulfur oxy-acids which are suitable for use as catalyst component (c) include the above sulfur oxy-acids which have an $-H_o$ of greater than 7.0.

Preferred catalysts in the process of this invention provide toluic acid comprised of at least 70 mol % p-toluic acid; especially preferred catalysts provide toluic acid comprised of at least 85 mol % p-toluic acid. Preferred catalysts, in addition to the preferences noted above, include those wherein catalyst ingredients (b) and (c) are the same and consist of a sulfur oxy-acid having an $-H_o$ greater than 7.0. The most preferred catalysts herein include those wherein the molar ratios (c/a) and (d/a) are at least 4 and 8, respectively, ingredient (a) is a compound of rhodium or iridium and the sulfur oxy-acid (c), and ingredients (b) and (c) are the same.

Sufficiently strong, that is, having an $-H_o$ of greater than 7.0, polymeric sulfonic acids also can be used in the process of the invention. Such acids are comprised of polymeric materials having sulfonic acid groups attached to the polymer structure. Representative of such a sulfonic acid is a perfluorinated polymeric sulfonic acid. Nafion ® Perfluorosulfonic Acid Products represent commercially available materials of this type. The use of Nafion ® as a strong acid is described in J. Org. Chem., 42, 4187 (1977) and 43, 3142 and 3147 (1978) in a series of papers by Olah et al. and Kaspi et al. and entitled "Heterogeneous Catalysis By Solid Superacids." It should be understood that the polymeric sulfonic acids useful in this invention normally provide catalyst ingredients (b) and (c). If, however, the sulfonic acid sites in the polymer have been largely or completely neutralized, i.e., converted to the salt form by the addition of a salt or hydroxide of a Group Ia or IIa metal, only catalyst ingredient (b) is provided by the polymer and a strong acid ingredient (c) must be added to obtain an operable catalyst. It will be obvious to one skilled in the art that when at least 0.5 mol % of the sulfonic acid or sulfonate salt sites in the polymer have reacted with the catalytically active rhodium or iridium ions, catalyst ingredient (a) is also provided by the polymer. Similarly, catalyst ingredient (d) can be provided by the polymer if sufficient polymer sites have reacted with the catalytically active copper. Catalysts prepared herein from a polymeric sulfonic acid are referred to as heterogeneous catalysts. Those prepared herein from the nonpolymeric sulfonic acid are referred to as homogeneous catalysts.

Included in this invention are perfluorinated polymeric sulfonic acids having, based on the sulfonic acid groups, about 5 to 98.5 mol % of hydrogen ions and 1.5 to about 95 mol % of rhodium or iridium and cupric ions, the molar ratio of cupric ions to rhodium or iridium ions being at least 0.5. Preferred polymeric sulfonic acids have 50 to 98.5 mol % of hydrogen ions and 1.5 to 50 mol % of the rhodium or iridium and copper ions, the molar ratio of cupric ions to rhodium or iridium ions being at least 4, more preferably at least 8. Also included in this invention are perfluorinated polymeric sulfonate salts having, based on the sulfonate groups, about 5 to 98.5 mol % of Group Ia or Group IIa metal ions and 1.5 to about 95 mol % of rhodium or iridium and cupric ions, the molar ratio of cupric ions to rhodium or iridium ions being at least 0.5.

The process of the invention is carried out at 110°–250° C., preferably 130°–200° C. At below 110° C. the reaction proceeds, but at slow rates. There is little, if any, advantage in operating the process above 250° C. Particularly if any catalyst component is a thermally unstable material, for example, as are some polymeric sulfonic acids, the upper limit of reaction temperature must be selected accordingly.

Although the reaction pressure is not critical to the process of the invention, generally it should be at least 500 psi (3.45 MPa). The upper limit of pressure is usually governed by the cost of the equipment needed to contain the reactant materials.

Preferably, in order to avoid the use and handling of an explosive reaction mixture, the amount of oxygen introduced into the system should not exceed 7.5 mol % of the combined amounts of carbon monoxide and oxygen in the system. If the reaction is carried out in a batch type operation, for example, in an autoclave, it may be desirable, in order to maintain the lowest possible level of oxygen, to introduce the initial charge of toluene and carbon monoxide before adding the oxygen. Carbon monoxide can then be added subsequently in such amounts as is necessary to maintain the desired reaction pressure as carbonylation takes place.

As is already evident from the above description, the reaction can be carried out in a batchwise or continuous mode of operation in a system which can be either homogeneous or heterogeneous, depending on whether or not the catalyst is soluble in the reaction medium. Although a solvent or liquid medium which is inert to oxidative carbonylation can be present during the reaction, it is not necessary in the process of the invention since the toluene itself serves as a solvent or liquid medium. Workup of the toluic acid from the reaction mixture can be carried out by conventional means. Heterogeneous catalyst can be removed by filtration of the reaction mixture. When a soluble catalyst is used, that is, when the system is homogeneous, the reaction mixture can be diluted with methylene chloride and extracted with aqueous sodium chloride, after which the methylene chloride layer can be evporated to recover to toluic acid.

In the following examples, the toluic acids which were produced were converted to trimethylsilyl esters by conventional techniques and then analyzed by means of standard gas chromatographic procedures. All of the oxidative carbonylation examples (Examples 1 to 11) and comparative experiments (Experiments S1 to S17) were carried out at 150° C. and 27.6 MPa pressure except for Example 7 and Experiment S4 which were carried out at 13.8 MPa pressure and Experiment S16 which was carried out at 180° C.

Procedure for Catalyst

Preparation Using Nafion ® Perfluorosulfonic Acid Resin

The heterogeneous catalysts were prepared by stirring, preferably at about 40° to 95° C., an aqueous solution of a soluble compound of rhodium or iridium and cupric copper (for example, the nitrate or chloride) with Nafion ® ($H^+$) (of equivalent weight 1100) either until the supernatant of the resultant slurry was colorless or for such time as was necessary to convert the desired number of acidic sites in the Nafion ® ($H^+$) to the cupric and rhodium or iridium metal salts. The formation of the metal salts can be followed by titrating the acid (for example, nitric acid or hydrochloric acid) liberated in the supernatant of the slurry. A specific example of the procedure follows.

Twenty-two g of Nafion ® ($H^+$) containing 20 m equiv of sulfonic acid groups in 450 ml of $H_2O$ was stirred with 0.54 g of $Rh(NO_3)_3 \cdot 2H_2O$ (1.66 mmoles Rh) and $Cu(NO_3)_2 \cdot 3H_2O$ (1.65 mmoles of Cu) at 95° C. for about 27 h. The resultant slurry was filtered and the orange resin was dried in a vacuum oven for about 3 h at about 100° C. The filtrate was titrated for liberated nitric acid (7.4 mmoles of $HNO_3$). The catalyst thus prepared contains $$\frac{1.66 \times 100}{1.66 + 1.65 + (20 - 7.4)} = 10.4 \text{ mol \% rhodium ions,}$$

$$\frac{1.65 \times 100}{1.65 + 1.66 + (20 - 7.4)} = 10.4 \text{ mol \% cupric ions, and}$$

$$\frac{(20 - 7.4)100}{(20 - 7.4) + 1.65 + 1.66} = 79.2 \text{ mol \% hydrogen ions.}$$

The mole % of rhodium in catalyst ingredient (a), as calculated by the formula given below for Examples 1–10, is $$\frac{1.66 \times 100}{1.66 + 1.65 + 20} = 7.1 \text{ mol \% rhodium ions.}$$

The mole % of copper in catalyst ingredient (d), similarly calculated, is $$\frac{1.65 \times 100}{1.65 + 1.66 + 20} = 7.1 \text{ mol \% cupric ions.}$$

Nafion ® ($H^+$) may be coverted to a salt form, for example, the Na salt, by a similar procedure wherein the resin is treated with an aqueous solution of sodium chloride or sodium nitrate. The salt form may be further treated with water-soluble rhodium or iridium and cupric compounds to replace the desired number of Na ions with ions of rhodium or iridium and copper.

Alternatively, Nafion ® ($H^+$) may be converted substantially to a salt of rhodium or iridium and copper by either of the above techniques, and an ppropriate strong acid may be added to provide the necessary catalyst ingredients (b) and/or (c), as discussed above.

Procedure for Shaker Tube Experiment With Heterogeneous Catalyst From Nafion ®

In a typical experiment, a shaker tube was flushed with $N_2$, charged with the catalyst prepared as described above, cooled, evacuated and charged with 80 to 120 ml of toluene. The tube was sealed and heated to reaction temperature. Carbon monoxide, then oxygen, and then more carbon monoxide was introduced into the tube until the desired pressure was reached. The mol percent of oxygen was 7.5. During the reaction time of two hours, the tube was repressurized with carbon monoxide as necessary to maintain pressure during carbonylation. After the tube was discharged, the catalyst was removed by filtration and the filtrate was analyzed for toluic acids.

Procedure for Shaker Tube Experiment With Homogeneous (Soluble) Catalyst

In a typical experiment, a shaker tube (Hastelloy-C or tantalum) is flushd with $N_2$, charged with (a) an appropriate rhodium or iridium compound, (b) a suitable sulfur oxy-acid or metal salt thereof, (c) a suitable sulfur oxy-acid or sulfur oxy-acid mixture having an $-H_o$ of greater than 7.0, (d) a cupric salt, and (e) 80 ml of toluene, cooled and evacuated. Alternatively, the rhodium or iridium compound can be reacted separately with excess sulfur oxy-acid or metal salt thereof and then charged to the shaker tube in place of the first two ingredients described above. After being charged the tube is sealed and heated to reaction temperature. Carbon monoxide, then oxygen, and then more carbon monoxide is introduced into the tube until the desired pressure is reached. The mol % of oxygen in the tube is no greater than 7.5. During the reaction time of two hours, the tube is repressurized with carbon monoxide as necessary to maintain pressure during carbonylation. Alternatively, the shaker tube is pressurized with a gaseous mixture of oxygen in carbon monoxide (mol % of oxygen is 3%) and then the mol % of oxygen is increased to 7.5% by the addition of oxygen. During the reaction time of two hours the tube is repressurized with carbon monoxide/oxygen mixture (3 mol % oxygen). After reaction the tube is discharged of the liquid contents and the recovered solution is diluted with $CH_2Cl_2$ and extracted with saturated aqueous NaCl solution. The organic phase is dried over $MgSO_4$, concentrated to a small volume, and then analyzed for toluic acids.

EXAMPLES 1–10

These examples represent various embodiments of the process of the invention, carried out using the procedures outlined above. Appropriate data for the examples using the homogeneous catalyst are summarized in Table 1, for the examples using the heterogeneous catalyst, in Table 2. At the end of each table are provided data relative to experimental showings (S) which were carried out to compare the process of the invention as claimed herein with similar processes outside the invention.

For the homogeneous systems, Experiments S1 to S6 (Table 1), show that, in the absence of catalyst ingredient (d), selectivity to p-toluic acid is maintained at a high level, but the yield of p-toluic acid is relatively low, unlike the present process which provides high yields of the p-isomer. Experiments S7 and S8 show that reduced forms of copper ($Cu^+$ and Cu metal) destroy catalyst effectiveness so that no toluic acids are produced. Experiment S9 shows that the use of cupric salt of a weak, non-sulfur-containing acid (acetic acid) fails to increase p-toluic acid yield and reduces selectivity to the p-isomer. Experiments S10 to S14, described separately below, show the ineffectiveness of other metal salts as replacements for cupric salts.

For the heterogeneous systems, Experiment S15 (Table 2) shows that a substantially reduced yield of p-toluic acid is obtained in the absence of catalyst ingredient (d). Experiment S16 shows that the presence of catalyst ingredient (a) is essential for catalytic activity.

In the following tables (Table 1, column 4; Table 2, columns 4, 5), the difference between the mol % metal (rhodium or iridium+copper, i.e. the total amount of catalyst ingredients (a) and (d)) and 100 mol % represents the mol % of catalyst ingredients (b)+(c). In Examples 1–4 and 6–10 (Tables 1 and 2), ingredients (b) and (c) are provided by the same compound. In Example 5 (Table 1), mol % of of ingredient (b), $CF_3SO_3Na$, is shown.

In the tables the mol % metal (rhodium or iridium and copper) shown is calculated using the formulae:

$$\text{mol \% rhodium or iridium} = \frac{n[\text{mols of }(a)]}{\text{mols of }(a + b + c + d)} \times 100;$$

$$\text{mol \% copper} = \frac{m[\text{mols of }(d)]}{\text{mols of }(a + b + c + d)} \times 100$$

where (a), (b), (c), and (d) are the catalyst ingredients defined above, n is the number of gram atoms of rhodium or iridium per mol of (a) and m is the number of gram atoms of copper per mol of (d).

Experiments S10 to S12 and Example 3 are similar, the difference being that the cupric salt (of Example 3) was replaced with $Mn(O_3SCF_3)_2$, $NiSO_4$ and $Fe_2(SO_4)_3$ in Experiments S10 to S12, respectively. Mol % manganese, nickel and iron was 28.9, 31.6, and 30.3, respectively; mol % rhodium was 1.4 in each experiment. Experiments S13 and S14 were similar to Example 9 except that the cupric salt was replaced with $Co(O_3SCF_3)_2$ and $Ce(SO_4)_2$, respectively. Mol % cobalt and cerium was 28.2 and 44.7, respectively; mol % rhodium was 2.8 in Experiment S13 and 2.2 in Experiment S14. In Experiments S10 to S14, selectivity to p-toluic acid was in the range 85 to 93 mol %, but the amount of p-toluic acid produced varied from nearly zero (cerium) to $2.6 \times 10^{-3}$ mol (manganese), indicating no significant improvement in p-isomer yield over that achieved with rhodium alone.

TABLE 1

| | Homogeneous Catalyst | | | | | | |
|---|---|---|---|---|---|---|---|
| | Catalyst Components | | | | | | p-Toluic Acid (mol × $10^3$) |
| Ex. or Exp. | Compound | Amount (mol × $10^3$) | Mol % Metal | Distribution (mol %) | | | |
| | | | | o | m | p | |
| 1 | $Rh_6(CO)_{16}$ | 0.19 | 1.7 | 0.6 | 3.9 | 95.4 | 14.8 |
| | $CuSO_4$ | 20.6 | 30.9 | | | | |
| | $CF_3SO_3H$ | 45.1 | | | | | |
| 2 | $Rh(NO_3)_3 \cdot 2H_2O$ | 0.92 | 1.1 | 2 | 7 | 91 | 13.3 |
| | $CuSO_4$ | 41.4 | 47.4 | | | | |
| | $CF_3SO_3H$ | 45.1 | | | | | |
| 3 | $Rh(NO_3)_3 \cdot 2H_2O$ | 0.92 | 1.4 | 2 | 9 | 89 | 7.9 |
| | $CuSO_4$ | 20.6 | 31.1 | | | | |
| | $CF_3SO_3H$ | 45.1 | | | | | |
| 4 | $Rh(NO_3)_3 \cdot 2H_2O$ | 0.92 | 1.7 | 2.5 | 8.5 | 89 | 7.8 |
| | $Cu(O_3SCF_3)_2$ | 9.1 | 16.5 | | | | |
| | $CF_3SO_3H$ | 45.1 | | | | | |
| 5 | $Rh(NO_3)_3 \cdot 2H_2O$ | 0.92 | 1.3 | 3 | 7 | 90 | 4 |
| | $Cu(O_3SCF_3)_2$ | 18.3 | 26.1 | | | | |
| | $NaO_3SCF_3$ | 5.8 | 8.3 | | | | |
| | $CF_3SO_3H$ | 45.1 | | | | | |
| 6 | $Rh(NO_3)_3 \cdot 2H_2O$ | 0.92 | 2.7 | 0.8 | 7.8 | 91.4 | 5.9 |
| | $Cu(O_3S\phi CH_3)_2$ | 9.85 | 28.9 | | | | |
| | $CH_3\phi SO_3H$ | 23.3 | | | | | |
| 7 | $Rh(NO_3)_3 \cdot 2H_2O$ | 0.92 | 1.6 | 0.8 | 6.5 | 92.7 | 3.9 |
| | $Cu(O_3S\phi CH_3)_2$ | 9.85 | 17.2 | | | | |
| | $CH_3\phi SO_3H$ | 46.5 | | | | | |
| 8 | $IrCl_3$ | 1.0 | 1.1 | 3 | 14 | 83 | 9.7 |
| | $CuSO_4$ | 41.3 | 47.3 | | | | |
| | $CF_3SO_3H$ | 45.1 | | | | | |
| 9 | $Rh(NO_3)_3 \cdot 2H_2O$ | 0.92 | 2.9 | 1 | 9 | 90 | 6.2 |
| | $Cu(O_3SCF_3)_2$ | 8.3 | 26.2 | | | | |
| | $CF_3SO_3H$ | 22.5 | | | | | |
| S1 | $Rh(NO_3)_3 \cdot 2H_2O$ | 0.92 | 1.8 | 2 | 9 | 89 | 1.5 |
| | $NaO_3SCF_3$ | 5.8 | 11.1 | | | | |
| | $CF_3SO_3H$ | 45.1 | | | | | |
| S2 | $Rh(NO_3)_3 \cdot 2H_2O$ | 0.92 | 1.9 | 2.2 | 6.4 | 91.4 | 2.5 |
| | $CF_3SO_3H$ | 45.1 | | | | | |
| S3 | $Rh(NO_3)_3 \cdot 2H_2O$ | 0.92 | 3.8 | 1 | 6 | 93 | 1.2 |
| | $CH_3\phi SO_3H$ | 23.3 | | | | | |
| S4 | $Rh(NO_3)_3 \cdot 2H_2O$ | 0.92 | 1.9 | 0.9 | 5.5 | 93.6 | 1.3 |
| | $CH_3\phi SO_3H$ | 46.5 | | | | | |
| S5 | $IrCl_3$ | 1.0 | 2.2 | 1.3 | 12.4 | 86.3 | 2.5 |
| | $CF_3SO_3H$ | 45.1 | | | | | |
| S6 | $Rh(NO_3)_3 \cdot 2H_2O$ | 0.92 | 3.9 | 1.2 | 6.4 | 92.3 | 1.8 |
| | $CF_3SO_3H$ | 22.5 | | | | | |
| S7 | $Rh(NO_3)_3 \cdot 2H_2O$ | 0.92 | 1.0 | 0 | 0 | 0 | 0 |
| | $Cu_2O$ | 41.7 | 47.5 | | | | |
| | $CF_3SO_3H$ | 45.1 | | | | | |
| S8 | $Rh(NO_3)_3 \cdot 2H_2O$ | 0.92 | 0.74 | 0 | 0 | 0 | 0 |
| | Cu | 78.1 | 62.9 | | | | |
| | $CF_3SO_3H$ | 45.1 | | | | | |
| S9 | $Rh(NO_3)_3 \cdot 2H_2O$ | 0.92 | 1.1 | 6.2 | 31 | 62.8 | 2.4 |
| | $Cu(OCOCH_3)_2$ | 36.3 | 44.1 | | | | |
| | $CF_3SO_3H$ | 45.1 | | | | | |

TABLE 2

| | Heterogeneous Catalyst | | | | | | |
|---|---|---|---|---|---|---|---|
| Ex. or Exp. | Prepared Catalyst (g) | Nafion ® Resin Form | Mol % Rh | Mol % Cu | Isomer Distri. ((mol %)) | | p-Toluic Acid (mol × $10^3$) |
| | | | | | o | m | p | |
| 10 | 4 | $H^+$ | 7.1 | 7.1 | 2 | 11 | 87 | 0.2 |
| S15 | 4 | $H^+$ | 14.5 | 0 | 1.5 | 12.5 | 86 | 0.08 |
| S16 | 3 | $H^+$ | 0 | 19.1 | 0 | 0 | 0 | 0 |

EXAMPLE 11

A sample of $Rh(OH)_3 \cdot H_2O$, prepared from $RhCl_3 \cdot 3H_2O$ by the procedure of Basolo, Inorganic Syntheses, VII, page 214, was reacted without external heating with a 3:1 molar excess of trifluoromethanesulfonic acid. Unreacted acid was distilled off under reduced pressure and a reddish-brown solid was recovered. Infrared analysis of the solid showed characteristic bands at 1250 $cm^{-1}$, 1176 $cm^{-1}$ and 1030 $cm^{-1}$, closely similar to the trifluoromethanesulfonate ion ($CF_3SO_3^-$) bands observed in various metal salts of trifluoromethanesulfonic acid by Gramstad and Haszeldine, J. Chem. Soc., 173 (1956), Haszeldine & Kidd, J. Chem. Soc., 4228 (1954), and Batchelor et al., Inorg. Chem., 16, 1414 (1977).

The rhodium salt, prepared as described above, was used as ingredient (a) in a homogeneous catalyst of this invention. The catalyst was used to prepare toluic acid according to the previously described shaker tube procedure for homogeneous systems. The results are given in Table 3. Also shown in Table 3 are the results of comparative Experiment S17 which is outside this invention. The comparison experiment has been included to show the effect of eliminating catalyst ingredient (d).

TABLE 3

| | Homogeneous Catalyst | | | | | | |
|---|---|---|---|---|---|---|---|
| | Catalyst Components | | | Isomer Distri. (mol %) | | | p-Toluic Acid |
| Ex. or Exp. | Compound | Amount (mol3 × 10³) | Mol % Metal | o | m | p | (mol × 10³) |
| 11 | $Rh(O_3SCF_3)_3$ | 0.55 | 0.9 | 1.1 | 9.9 | 89 | 29.3 |
| | $CuSO_4$ | 37.5 | 61.9 | | | | |
| | $CF_3SO_3H$ | 22.5 | | | | | |
| S17 | $Rh(O_3SCF_3)_3$ | 0.55 | 2.4 | 2 | 9 | 89 | 1.8 |
| | $CF_3SO_3H$ | 22.5 | | | | | |

Best Mode For Carrying Out The Invention

The best mode for carrying out the process of the invention is believed to be demonstrated by Examples 11, 1, 2 and 10.

Industrial Applicability

Toluic acid, particularly p-toluic acid, is an important intermediate in the preparation of terephthalic acid which is used in the manufacture of fiber-forming polyesters.

Although the preferred embodiments of the invention have been illustrated and described, it is to be understood that there is no intent to limit the invention to the precise construction herein disclosed and that the right is reserved to all changes and modifications within the scope of the invention as defined in the appended claims.

I claim:

1. Process for oxidatively carbonylating toluene to toluic acid, at least 50 mol % of the toluic acid being the p-isomer, said process comprising contacting and reacting, at 110°–250° C., at a pressure of at least 500 psi (3.45 MPa), toluene, carbon monoxide, oxygen and the catalyst ingredients consisting essentially of
   (a) a compound of rhodium or iridium;
   (b) a sulfur oxy-acid or a Group Ia or IIa metal salt of a sulfur oxy-acid;
   (c) a sulfur oxy-acid or sulfur oxy-acid mixture having a Hammett acidity value ($-H_o$) of greater than 7.0; and
   (d) a cupric salt of a sulfur oxy-acid; said catalyst ingredients containing 0.3–30 mol % of (a) and 70–99.7 mol % of (b+c+d), with the molar ratios (b/a) and (c/a) each being at least 2 and the molar ratio (d/a) being at least 0.5, and recovering toluic acid.

2. The process of claim 1 wherein at least 70 mol % of the toluic acid is p-isomer, the molar ratios (b/a) and (c/a) each being at least 3 and the molar ratio (d/a) being at least 4.

3. The process of claim 1 wherein at least 85 mol % of the toluic acid is p-isomer and catalyst ingredients (b) and (c) are the same and consist of a sulfur oxy-acid having an $-H_o$ greater than 7.0.

4. The process of claim 3 wherein each of the molar ratios (b/a) and (c/a) is at least 4 and the molar ratio (d/a) is at least 8.

5. Process of claim 1 wherein the catalyst is a homogeneous catalyst.

6. Process of claim 5 wherein the catalyst ingredients (b) and (c) are the same and consist of a sulfur oxy-acid having an $-H_o$ greater than 7.0.

7. Process of claim 6 wherein the sulfur oxy-acid is trifluoromethanesulfonic acid.

8. Process of claim 6 wherein the sulfur oxy-acid is p-toluenesulfonic acid.

9. Process of claim 6 wherein the sulfur oxy-acid is perfluorooctanesulfonic acid.

10. Process of claim 1 wherein the catalyst is a heterogeneous catalyst.

11. Process of claim 10 wherein (b) and (c) are the same and consist of a perfluorinated polymeric sulfonic acid.

12. Process of claim 1 wherein (a) is rhodium nitrate.

13. Process of claim 1 wherein (a) is $Rh_6(CO)_{16}$.

14. Process of claim 1 wherein (a) is $Rh(O_3SCF_3)_3$.

15. Process of claim 1 wherein (a) is iridium chloride.

16. Process of claim 1 wherein (d) is $CuSO_4$.

17. Process of claim 1 wherein (d) is $Cu(O_3SCF_3)_2$.

18. Process of claim 1 wherein (d) is cupric p-toluene sulfonate.

19. Process of claim 1 wherein the temperature is 130°–200° C.

20. Process of claim 1 wherein the catalyst ingredients (a), (b), (c) and (d) are provided by the perfluorinated polymeric sulfonic acid having, based on the sulfonic acid groups, about 5 to 98.5 mol % of hydrogen ions and 1.5 to about 95 mol % of rhodium or iridium and cupric ions.

21. Process of claim 20 wherein the perfluorinated polymeric sulfonic acid has, based on the sulfonic acid groups, 50 to 98.5 mol % of hydrogen ions and 1.5 to 50 mol % of rhodium or iridium and cupric ions, the molar ratio of cupric ions to rhodium or iridium ions being at least 4.

22. Process of claim 1 wherein the catalyst ingredients (a), (b) and (d) are provided by the perfluorinated polymeric sulfonate salt having, based on the sulfonate groups, about 5 to 98.5 mol % of Group Ia or Group IIa metal ions and 1.5 to about 95 mol % of rhodium or iridium and cupric ions.

* * * * *